(12) United States Patent
Laskavy

(10) Patent No.: US 12,076,389 B2
(45) Date of Patent: Sep. 3, 2024

(54) AGENT FOR THE PREVENTION OF VIRAL INFECTIONS

(71) Applicants: Vladislav Nikolaevich Laskavy, Saratov (RU); Sergei Ivanovich Ivanenko, Oberwill b. Zug (CH)

(72) Inventor: Vladislav Nikolaevich Laskavy, Saratov (RU)

( * ) Notice: Subject to any disclaimer, the term of this patent is extended or adjusted under 35 U.S.C. 154(b) by 771 days.

(21) Appl. No.: 17/250,007

(22) PCT Filed: Apr. 18, 2019

(86) PCT No.: PCT/RU2019/000259
§ 371 (c)(1),
(2) Date: Jan. 13, 2021

(87) PCT Pub. No.: WO2019/216791
PCT Pub. Date: Nov. 14, 2019

(65) Prior Publication Data
US 2021/0308251 A1 Oct. 7, 2021

(30) Foreign Application Priority Data

May 7, 2018 (RU) ................................ 2018116987
Apr. 18, 2019 (WO) .............................. 2019/000259

(51) Int. Cl.
| | | |
|---|---|---|
| A61K 39/145 | (2006.01) |
| A61K 39/225 | (2006.01) |
| A61K 39/385 | (2006.01) |
| A61K 39/39 | (2006.01) |
| A61K 47/54 | (2017.01) |
| A61K 47/60 | (2017.01) |
| A61K 47/69 | (2017.01) |
| A61P 31/16 | (2006.01) |
| A61K 39/00 | (2006.01) |

(52) U.S. Cl.
CPC .......... *A61K 39/145* (2013.01); *A61K 39/225* (2013.01); *A61K 39/385* (2013.01); *A61K 39/39* (2013.01); *A61K 47/542* (2017.08); *A61K 47/60* (2017.08); *A61K 47/6901* (2017.08); *A61K 47/6905* (2017.08); *A61P 31/16* (2018.01); *A61K 2039/55505* (2013.01); *A61K 2039/60* (2013.01)

(58) Field of Classification Search
None
See application file for complete search history.

(56) References Cited

FOREIGN PATENT DOCUMENTS

| | | | | |
|---|---|---|---|---|
| RU | 2354695 C1 | 5/2009 | | |
| RU | 2393871 C1 | 7/2010 | | |
| RU | 2429875 C2 | 9/2011 | | |
| RU | 2463073 C1 * | 10/2012 | ............ | A61K 39/12 |
| RU | 2505306 C2 | 1/2014 | | |
| RU | 2549495 C1 | 4/2015 | | |

OTHER PUBLICATIONS

English language translation of RU 2463073 C1 (Publ. Oct. 10, 2012). (Year: 2012).*

* cited by examiner

*Primary Examiner* — Dominic Lazaro
(74) *Attorney, Agent, or Firm* — Aird & McBurney LP

(57) ABSTRACT

The invention relates to medicine and veterinary medicine, and more specifically to pharmacology, and can be used to prevent viral infections caused be RNA viruses that have a lipid capcid. An agent for prevention viral infections comprises viral material from RNA viruses that have a lipid capcid and stabilized colloidal selenium at a 1:1 ratio. The viral material from RNA viruses has titres of 6.0-8.0 lg $TCD_{50/ml}$. To obtain colloidal selenium having particle sizes from 10 to 15 nm the colloidal selenium is stabilized with polyethylene glycol, and for colloidal selenium having particle sizes from 20 to 40 nm, the colloidal selenium is stabilized with cysteine.

3 Claims, No Drawings

AGENT FOR THE PREVENTION OF VIRAL INFECTIONS

CROSS-REFERENCE TO RELATED APPLICATIONS

The instant application is a National Phase Entry of International Patent Application No. PCT/RU2019/000259, filed on Apr. 18, 2019, and claims priority to Russian Patent Application No. 2018116987, filed on May 7, 2018, the entire specifications of both of which are expressly incorporated herein by reference.

FIELD OF THE INVENTION

The invention relates to medicine and veterinary medicine, and more specifically, to pharmacology, and can be used for prevention of viral infections caused by RNA-containing viruses with a lipid capsid, in particular, of influenza, transmissible porcine gastroenteritis and other viral infections. The invention expands the range of agents with the stated intended purpose.

BACKGROUND OF THE INVENTION

Flu and cold are the most common viral infections in humans. Every year, approx. 10%-20% of the world's population gets the flu, and the common cold is the most common infection in humans.

There are many non-specific drugs for the prevention of viral infections, for example, Grippferon, Arbidol, Acyclovir. Along with the widely used non-specific preventive drugs, new ones are being developed on the basis of plants (RF patent No. 2505306, 2393871), mycelium (RF patent No. 2522880), dipeptide (RF patent No. 2429875), etc.

In particular, such anti-viral agent is known (see RF patent No. 2505306 in class IPC A61K 36/185, published on 27 Jan. 2014), containing an aqueous extract of leaves and branches of *Ribes* plants. The product is intended for use in viral infections, including colds with the primary infection caused by rhinoviruses, adenoviruses and/or coronaviruses, influenza, and viral infection caused by retroviruses.

Since the agent is a plant extract, it is a multi-component system that can show not only positive effects on viruses but also change the resistance of the human body and animals.

Another group of preventive drugs is specific drugs (vaccines).

A common feature of all existing vaccines is that they act on a specific serotype of the pathogen and its antigenic composition.

In particular, there is a known remedy for the prevention of viral infections based on a cold-adapted strain of influenza A virus/Krasnodar/101/59/35 (H2N2) (see RF patent No. 2354695 for class IPC C12N 7/00, published on 10 May 2009) containing this strain in ten-fold dilution, 1% chitosan glutamate solution and 0.9% sodium chloride solution.

However, the drug works against a certain virus type (H2N2) only. Moreover, the effect of this live vaccine is not directed at the virus itself, but at strengthening the human body immune response.

The closest to the claimed product is the agent for prevention of viral infections, in particular, transmissible gastroenteritis in pigs (see RF patent No. 2463073 for class IPC A61K 39/225 published on 10 Oct. 2012), containing viral material from the VN-96 strain of pig transmissible gastroenteritis virus in a titer of 7.0-7.2 lg TCD50/ML and saline solution in certain percentages.

However, this agent is aimed at preventing transmissible gastroenteritis of a certain pathogen serotype only and is ineffective in immunodeficiency conditions of animals.

Thus, these equivalents do not solve the problem of the virus intracellular suppression but only contribute to the immunity correction. The creation of antiviral drugs is far from a solved task. Therefore, the search for new protection agents against viral infections is very relevant.

SUMMARY OF THE INVENTION

The technical problem of the claimed invention is the expansion of the range of antiviral preventive drugs and the formation of new approaches to prevention of human viral diseases, especially influenza, due to the intracellular virus suppression.

The technical result achieved in this case is to create a simple and inexpensive agent for the prevention of viral diseases of humans and animals caused by RNA-containing viruses with a lipid capsid, which enables to quickly prevent viral diseases at minimal cost (by a single or double injection), regardless of the virus serotypes (the pathogen type) and its antigenic composition by activating the completed phagocytosis of viruses, without increasing the titer of specific viral neutralizing antibodies.

To achieve the stated result, the agent for the prevention of viral infections has been proposed that contains viral material from RNA-containing viruses with a lipid capsid and stabilized colloidal selenium.

The ratio of the weight parts of the viral material to the stabilized colloidal selenium is 1:1. Viral material from RNA-containing viruses has titers of 6.0-8.0 lg TCD50/ML.

To obtain colloidal selenium with particle sizes of 10 nm to 15 nm, colloidal selenium is stabilized with polyethylene glycol, and colloidal selenium with particle sizes of 20 nm to 40 nm, with cysteine.

Stabilized colloidal selenium has a concentration of 6.0%-6.2%.

The sources of patent and scientific and technical documents known to the authors do not describe the agent for prevention of viral infections based on viral material and stabilized colloidal selenium taken in equal parts, which allows for the prevention of viral diseases regardless of the pathogen type and its antigenic composition, by activating completed phagocytosis and, as a result, intracellular virus suppression.

According to the authors, selenium with particle sizes of 10 nm-40 nm is able to be absorbed by phagocytic cells. Colloidal selenium particles protect the lipid capsid of the virus from the effects of macroorganism cell enzymes. The phagocyte captures the selenium-virus complexes and exposes them to "digestion" due to the created volume for capturing (phagocytic) virus particles that have become commensurable with bacteria. This allows delivering all the structural elements of the virus (lipids, proteins, RNA) to phagocytic cells, which contributes to complete immune response and the development of phagocyte "memory" for further protection of the macroorganism from viral infections.

Selenium is known to be a natural metabolite (see, for example, http://ru.wikipedia.org/wiki; http://www.zdoroveplus.ru/page315.html; 23 involved in the biochemical processes of the body. As a natural metabolite, it does not accumulate in cells but is used as an activator of metabolic processes in phagocytes.

It is colloidal selenium with particle sizes of 10 nm-40 nm in combination with viral particles that is a unique stimulator of the immune defence of the macroorganism at the level of specific completed phagocytosis.

Thus, the authors for the first time established a non-obvious property consisting in the participation of phagocytes in the immune defence against viral infections. The claimed invention is based on new immune protection by the participation of phagocytes in the immune process in viral infections, no increase in antibodies to pathogens and the "memory" in phagocytic cells.

That is, there is protection, but there are no antibodies, or they are formed in minimal quantities.

This allows us to conclude that the claimed solution has the "inventive level" criterion. Colloidal selenium is nanoscale particles of selenium in solution (see, for example, http://testvich.ru/entsiklopediya/kolloidnyiy-selen-zoloto). Colloidal selenium is obtained by reducing dilute aqueous solutions of soluble selenium with sulfur oxide (IV), hydrazine hydrate, dextrose, titanium trichloride, or by passing an electric current through a solution of selenic acid (the anode is platinum, the cathode is coated with selenium), as well as by other methods. The color of colloidal selenium depends on the deposition conditions and varies from purple to red; the density is the same as that of powdered selenium (see, for example, http://ibrain.kz/himiya-svoystva-elementov/selen).

It is well known (see, for example, http://texnosila.narod.ru/Foton/nanoteh/Exampl KOAKR3.html) that colloidal solutions have unstable properties. Unstable properties are determined by many factors—temperature, solution density, material, number and size of particles, external influences, such as the base vibration, the electromagnetic fields, radiation. All these factors significantly affect the equilibrium state of the colloid medium.

The claimed invention used as stabilizing factors the addition of selenium or polyethylene glycol (where the size of selenium particles in the solution is 10 nm-15 nm) or cysteine (where the size of selenium particles is 20-40 nm), or milk serum protein (where the size of particles is 100 nm and above) to a colloidal solution. At the same time, the choice of a particular stabilizer was carried out experimentally, depending on the technology of preparation of the drug.

The viral material was obtained by cultivating strains: vector-borne gastroenteritis and influenza virus. The strain of vector-borne gastroenteritis virus, VN-96, is deposited in the Russian State Center for Animal Feed and Drug Standardization and Quality (VGNKI) (deposit certificate No. 1103/19 dated May 27, 2009). Isolated in 1988 from the RIMS vaccine strain on the SPEV transferable culture (large-scale version), a virulent for pigs, the virus titer is 7.0 lg TCD50/ml.

Influenza A virus strain/Krasnodar/101/3 5/59 (H2N2) is registered in the collection of the D. I. Ivanovsky Research Institute of Virology (No. 2439 dated 9 Jun. 2008). It is intended as an attenuation donor strain for obtaining reassortant live influenza vaccines (see RF patent No. 2354695). The strain obtained by serial passages in chicken embryos and the MDCK cell culture at low temperature with the subsequent 3-fold cloning method of plaques in the MDCK cell culture that ensures genetic homogeneity of the strain.

The agent for the prevention of viral infections is a solution of red-brown color, odorless.

DETAILED DESCRIPTION

To obtain the viral material, the original strain of the virus (in particular, VN-96 virus strain of transmissible gastroenteritis, influenza A virus strain/Krasnodar/101/35/59 (H2N2), with a specific title, is taken and brought to the titer of 6.0-8.0 lg TCD50/ml.

For the prevention of influenza, a viral material with a titer of 8.0 lg TCD50/ml is preferred, and for the prevention of transmissible gastroenteritis, with a titer of 7.0 lg TCD50/ml.

Viral material is stored at −18° C. to −20° C.

The invention is illustrated by the following examples.

Example 1. Example of preparation of colloidal selenium with a particle size of 10 nm-15 nm. 100 mg sodium selenite containing 40 mg selenium is taken and dissolved in 10 ml distilled water. 0.52 g hydrochloric acid hydrozine is taken and dissolved in 5 ml distilled water. 10 ml sodium selenite is added to the conical flask, and 5 ml hydrozine is immediately added.

The solution is mixed on a magnetic stirrer at 450 rpm without heating until an intense brick-red color appears (precipitation of amorphous selenium) for 10 minutes.

The flask is filled with 10 ml polyethylene glycol (PEG-200), and the mixture is heated to 150° C. with intensive stirring until the water completely evaporates (boiling ceases).

After the water has evaporated, a deflegmator is placed on the flask and the temperature is raised to 220° C. for 15-30 minutes. The mixture is cooled to room temperature.

The mixture is centrifuged at 4200 rpm for 20 minutes. The add-on is placed on dialysis against a pH 7.2 phosphate-salt buffer.

The resulting mixture is concentrated on a rotary evaporator with a vacuum at 70° C. and a rotation speed of 50 vol./min. (25 ml of the mixture is concentrated to 15 ml). Then a saline solution is added to the resulting sediment until a colloidal selenium concentration of 0.062 mg/ml (6.2%) is obtained.

The size of selenium particles determined using the LIBRA 120 electron microscope (Carl Zeiss, Germany) was 10 nm-15 nm.

Example 2. Example of preparation of colloidal selenium with a particle size of 20 nm-40 nm. 0.001 M selenic acid ($H_2SeO_3$) is added drop by drop to 0.01 M L—cysteine solution with constant stirring at room temperature in a volume ratio of 1:1.

Then saline solution is added to the resulting sediment until a colloidal selenium concentration of 0.062 mg/ml (6.2%) is obtained. The size of selenium particles determined using the LIBRA 120 electron microscope (Carl Zeiss, Germany) was 20 nm-40 nm.

Example 3. Example of preparation of colloidal selenium with a particle size of 100 nm-140 nm. This colloidal selenium was also used in further experiments to obtain a preventive agent to prove the achieved result efficacy.

0.5 ml of 1 M hydrochloric acid hydrazine solution and 0.125 ml of 1 M sodium selenite (rapidly developing yellow-orange color) are added to 2 mL distilled water. Within 30 seconds, this solution is added to the milk serum protein.

The mixture is mixed for 1 hour. After the orange staining appears, the reaction is stopped with a 1M solution of sodium hydroxide, by adjusting pH to 7.62. The resulting solution is dialyzed against a 0.01 M phosphate-salt buffer, than the mixture is concentrated.

Then a saline solution is added to the resulting sediment until a colloidal selenium concentration of 0.060 mg/ml (6.0%) is obtained.

The size of selenium particles determined using the LIBRA 120 electron microscope (Carl Zeiss, Germany) was 100 nm-140 nm.

The concentration of colloidal selenium (6.0-6.2%) obtained in Examples 1-3 provides a stable state of the selenium substance with particle sizes of 10 nm-140 nm. It has been shown experimentally that a selenium concentration of less than 6.0% and more than 6.2% leads to a violation of the required selenium particle size or selenium coagulation.

Example 4. The agent for the prevention of viral infections is prepared as follows.

1 ml viral material is taken from the VN-96 strain of the pig transmissible gastroenteritis virus in a titer of 7.0 lg TCD50/ml, to which 1 ml stabilized colloidal selenium with a particle size of 20 nm-40 nm is added, the resulting mixture is mixed.

The finished agent for the prevention of viral infections is a red-brown liquid.

Similarly to the one described in Example 4, viral material is prepared from influenza A virus strains/Krasnodar/101/35/59 (H2N2).

Example 5. Justification of the preventive properties of the claimed anti-flu drug.

In the experiment, 70 white mice were used, they were allocated in 7 groups (10 animals in each), of which 2 were the reference group and 5, the test groups. In the first reference group, the mice were not immunized. In the second reference group, mice were immunized subcutaneously with a drug containing 0.1 ml saline solution and 0.1 ml influenza A virus strain/Krasnodar 101/35/59 (H2N2)—with a titer of 8.0 lg TCD50/ml. The drug was administered twice with an interval of 14 days. In all test groups, the drug was also administered subcutaneously twice with an interval of 14 days between injections.

At the same time, in the first test group, mice were immunized with a drug containing 0.1 ml colloidal selenium with a particle size of 10 nm-15 nm, stabilized with polyethylene glycol (PEG), and 0.1 ml viral material from the influenza A virus strain/Krasnodar/101/35/59 (H2N2)—with a titer of 8.0 lg TCD50/ml.

In the second test group, mice were immunized with a drug containing 0.1 ml cysteine-stabilized colloidal selenium with a particle size of 20 nm-40 nm and 0.1 ml viral material from the influenza A virus strain/Krasnodar/101/35/59 (H2N2)—with a titer of 8.0 lg TCD50/ml.

In the third test group, mice were immunized with a preparation containing 0.1 ml colloidal selenium stabilized with milk serum protein with a particle size of 100 nm-140 nm and 0.1 ml viral material from the influenza A strain/Krasnodar/101/35/59 (H2N2)—with a titer of 8.0 lg TCD50/ml.

In the fourth and fifth test groups, mice were immunized with a preparation containing 0.1 ml cysteine-stabilized colloidal selenium with a particle size of 20 nm-40 nm and 0.1 ml viral material from the influenza A strain/Krasnodar/101/35/59 (H2N2), with a titer of 7.0 lg TCD50/ml (group four) and a titer of 6.0 lg TCD50/ml (group five).

28 days after the first administration of the drug, all groups of mice were infected with the intranasally virulent strain A/Brisbane/59/07 (H1N1) at a dose of 2.0 lg TCD50/0.05 ml.

72 hours after infection with the virulent strain, the mice were killed in accordance with the ethical principles of handling laboratory animals. The lungs of the mice were extracted and a 10% suspension was prepared in mortars with grated glass. 10-fold dilutions of this suspension were introduced into 9-day-old chicken embryos. After 48 hours of incubation of infected chicken embryos at 37° C. in the thermostat, the embryos were placed in the refrigerator at 4° C. for 18-24 hours.

Then the embryos were opened, allantois fluid was sucked out, and the titer of viruses in the lungs of each group of mice was determined using a hemagglutination reaction. The results are presented in Table 1.

TABLE 1

| Mice group name | Preparation composition | | Infectious titer of strain A/ Brisbane/59/ 07 (H1N1) in the lungs of immunized mice | Antibody titer for the strain A/ Krasnodar/ 101/35/59 vIFA |
|---|---|---|---|---|
| | Viral material from strain A/Krasnodar/ 101/35/ 59 (H2N2) | Stabilized colloidal selenium | | |
| 1 reference group | Non-immunized mice | | 4.5 lg $TCD_{50}$/ 0.2 ml | — |
| 2 reference group | with a titer of 8.0 lg $TCD_{50/ml}$ in the amount of 0.1 ml | saline in the amount of 0.1 ml | 5.0 lg $TCD_{50}$/ 0.2 ml | 640 |
| 1 test group | with a titer of 8.0 lg $TCD_{50/ml}$ in the amount of 0.1 ml | With a particle size of 10-15 nm in an amount of 0.1 ml | 3.0 lg $TCD_{50}$/ 0.2 ml | 1280 |
| 2 test group | with a titer of 8.0 lg $TCD_{50/ml}$ in the amount of 0.1 ml | With a particle size of 20-40 nm in an amount of 0.1 ml | 1.0 lg $TCD_{50}$/ 0.2 ml | 160 |
| 3 test group | with a titer of 8.0 lg $TCD_{50/ml}$ in the amount of 0.1 ml | With a particle size of 100- 140 nm in an amount of 0.1 ml | 4.5 lg $TCD_{50}$/ 0.2 ml | 640 |
| 4 test group | with a titer of 7.0 lg $TCD_{50/ml}$ in the amount of 0.1 ml | With a particle size of 20-40 nm in an amount of 0.1 ml | 1.0 lg $TCD5_{50}$/ 0.2 ml | 80 |
| 5 test group | with a titer of 6.0 lg $TCD_{50/ml}$ in the amount of 0.1 ml | With a particle size of 20-40 nm in an amount of 0.1 ml | 1.0 lg $TCD_{50}$/ 0.2 ml | 80 |

Table 1 shows that the titer of the virulent strain A/Brisbane/59/07 (NSH1) in the lungs of non-immune mice (reference group 1) was 4.5 lg TCD50/0.2 ml.

The titer of the virulent strain A/Brisbane/59/07 (NSH1) in the lungs of mice immunized subcutaneously with a dose of the influenza A strain/Krasnodar/101/35/59 (H2N2) with a titer of 8.0 lg TCD50/ml did not differ much from that in the first reference group—5 lg TCD50/0.2 ml.

However, there was a marked decrease in the titer of the virulent a/Brisbane/59/07 strain (H1N1) in the lungs of mice immunized subcutaneously with the same dose of the influenza strain A/Krasnodar/101/35/59 (H2N2) in combination with colloidal selenium. At the same time, when immunized with a drug with a particle size of 10 nm-15 nm, the titer was 3 lg TCD50/0.2 ml, and when immunized with a drug with a particle size of 20 nm-40 nm, a thousand-fold titer decrease was observed.

There was no decrease in the infectious titer of the virulent strain A/Brisbane/59/07 (H1N1) in the lungs of mice immunized subcutaneously with a drug with the stabilized colloidal selenium particle size of 100 nm-140 nm.

Studies on the use of viral material from the influenza strain A/Krasnodar/101/35/59 (H2N2) with the titers 7.0 lg TCD50/ml and 6.0 lg TCD50/ml in combination with stabilized colloidal selenium with particle sizes of 20 nm-40 nm have shown (see Table 1) that the drug with such a component content does not significantly increase the titers of specific viral neutralizing antibodies (the titer is 80) but provides effective protection against infection.

The results of studies presented in Example 5 to determine the protection efficacy when infecting mice with a virulent influenza strain prove that the best protection efficacy is achieved by introducing a drug containing stabilized colloidal selenium with particle sizes of 20 nm-40 nm and a viral material with a titer of 6.0-8.0 lg TCD50/ml.

Further studies to justify effective protection against transmissible gastroenteritis were conducted using a preparation containing stabilized colloidal selenium with particle sizes of 20 nm-40 nm and viral material against transmissible gastroenteritis with a titer of 8.0 lg TCD50/ml.

Since Example 5 (see Table 1) demonstrated that the anti-influenza protection efficacy correlates with a reduced, rather than an increased content of specific virus-neutralizing antibodies to influenza, the protection efficacy against transmissible gastroenteritis was assessed by the specific virus-neutralizing antibodies to transmissible gastroenteritis in laboratory animals, in mice and guinea pigs, and not by direct infection.

Example 6. Justification of the preventive properties of the claimed drug against transmissible gastroenteritis. 3 groups of Guinea pigs were formed to prove protection efficacy: 5 animals in each group.

One group of animals was a reference group, saline solution at 0.5 ml dose was administered to them only.

The first experimental group of animals was injected with viral material from the strain of transmissible gastroenteritis virus, VN-96, with a titer of 7.0 lg TCD50/ml in combination with a saline solution (0.25 ml viral material and 0.25 ml saline solution).

The second experimental group was injected with viral material from the strain of transmissible gastroenteritis virus, VN-96, with a titer of 7.0 lg TCD50/ml in combination with stabilized colloidal selenium (0.25 ml viral material and 0.25 ml colloidal selenium) with a particle size of 20 nm-40 nm, taken in a ratio of 1:1.

28 days after administration of the drugs, the titer of specific virus-neutralizing antibodies in the neutralization reaction was determined. The result is shown in Table 2.

TABLE 2

| Animal group name | Properties of the administered drug | Titer of specific viral neutralizing antibodies |
| --- | --- | --- |
| Reference | Saline solution | 0 |
| 1 test group | Viral material from the VN-96 strain, with a titer of 7.0 lg TCD50/ml | 1:128 |
| 2 test group | Viral material from the VN-96 strain with a titer of 7.0 lg TCD50/ml + stabilized colloidal selenium with particle sizes of 20 nm –40 nm | 1:8 |

Table 2 shows that the introduction of a drug containing viral material from the VN-96 strain with a titer of 7.0 lg TCD50/ml in combination with stabilized colloidal selenium with particle sizes of 20 nm-40 nm reduces the titer of specific virus neutralizing antibodies from 1:128 to 1:8, i.e. by 16 times.

Thus, the claimed agent for the prevention of viral diseases in humans and animals caused by RNA—containing viruses with a lipid capsid enables to quickly prevent viral diseases at minimal cost (by a single or double injection), regardless of the virus serotypes (pathogen varieties) and its antigenic composition, by activating the completed phagocytosis of viruses without increasing the titer of specific.

The claimed agent expands the range of antiviral preventive drugs and enables to solve the problem of preventing human viral diseases, especially influenza, due to intracellular virus suppression.

What is claimed is:

1. An agent for immunizing against influenza or transmissible porcine gastroenteritis,
    wherein the agent contains:
    (i) RNA-containing viruses with a lipid capsid; and
    (ii) stabilized colloidal selenium, which has particle sizes of 10 nm to 40 nm;
    wherein the RNA-containing viruses have a titer of 6.0 1 g TCD 50/ml to 8.0 1 g TCD 50/ml;
    wherein the stabilized colloidal selenium is in saline solution at a concentration of 6.0% to 6.2%; and
    wherein a ratio of weight parts of the RNA-containing viruses to the stabilized colloidal selenium in saline solution is 1:1.

2. The agent according to claim 1, wherein the agent contains the stabilized colloidal selenium with particle sizes of 10 to 15 nm stabilized by polyethylene glycol.

3. The agent according to claim 1, wherein the agent contains the stabilized colloidal selenium with particle sizes of 20 to 40 nm stabilized by cysteine.

* * * * *